(12) United States Patent
Sten-Nilsen

(10) Patent No.: US 12,419,610 B2
(45) Date of Patent: Sep. 23, 2025

(54) METHODS AND SYSTEMS FOR PULSE CIRCUITS OF ULTRASOUND TRANSDUCERS

(71) Applicant: GE Precision Healthcare LLC, Milwaukee, WI (US)

(72) Inventor: Bjornar Sten-Nilsen, Horten (NO)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 1005 days.

(21) Appl. No.: 17/450,432

(22) Filed: Oct. 8, 2021

(65) Prior Publication Data

US 2023/0112088 A1    Apr. 13, 2023

(51) Int. Cl.
*H10N 30/80*    (2023.01)
*A61B 8/00*    (2006.01)
*B06B 1/02*    (2006.01)
*G01S 7/52*    (2006.01)
*H10F 39/18*    (2025.01)

(52) U.S. Cl.
CPC .......... *A61B 8/4483* (2013.01); *B06B 1/0215* (2013.01); *G01S 7/5208* (2013.01); *H10F 39/18* (2025.01); *H10N 30/802* (2023.02)

(58) Field of Classification Search
CPC .............................. A61B 8/4483; H10N 30/802
USPC .................................................. 327/108–112
See application file for complete search history.

(56) References Cited

U.S. PATENT DOCUMENTS

2014/0266396 A1*  9/2014  Berzins .............. H03K 19/0963
                                                            327/399

* cited by examiner

*Primary Examiner* — Tomi Skibinski
(74) *Attorney, Agent, or Firm* — McCoy Russell LLP

(57) ABSTRACT

Various methods and systems are provided for a pulse circuit of a transmitter of an ultrasound system. In one example, the system may include a pulse circuit with transistors driving an ultrasound transducer of the ultrasound system, whereby the switching on and off of the transistors is mediated via one or more dynamic currents flowing from the gates of one or more of the transistors.

19 Claims, 4 Drawing Sheets

METHODS AND SYSTEMS FOR PULSE CIRCUITS OF ULTRASOUND TRANSDUCERS

FIELD

Embodiments of the subject matter disclosed herein relate to pulse circuits for ultrasound transducers of an ultrasound system.

BACKGROUND

Ultrasound, for medical or industrial applications, is an imaging modality that employs ultrasound waves to probe the acoustic properties of a target object (e.g., the body of a patient) and generate a corresponding image. Generation of sound wave pulses and detection of returning echoes is typically accomplished by an ultrasound probe having an array of transducers. Such transducers typically include electromechanical elements capable of converting electrical energy into mechanical energy for transmission of ultrasonic waves into the target object (e.g., patient tissue) and mechanical energy back into electrical energy when the reflected ultrasonic waves reach the transducers.

An ultrasound transducer may include a transmitter circuit (herein also referred to as "pulse circuit"), the transmitter circuit configured to generate ultrasonic acoustic pulses from the ultrasound transducer, and a receiver circuit, the receiver circuit configured to receive ultrasonic acoustic pulses at the ultrasound transducer. The pulse circuit is configured to convert electrical pulses generated by an electrical waveform generator into ultrasonic acoustic pulses via the transducer during ultrasound imaging. In other words, the pulse circuit may take as input one or more periodic electrical signals (e.g. spike pulses, square wave pulses, etc.) generated with a given maximum amplitude voltage, amplify the one or more periodic electrical signals, and output one or more transmit pulses for ultrasound imaging via the ultrasound transducer.

BRIEF DESCRIPTION

In one embodiment, a method comprises an ultrasound system comprising: an ultrasound transducer configured to generate acoustic ultrasonic pulses in response to electronic driving, a pulse circuit electrically coupled to and configured to drive the ultrasound transducer, the pulse circuit further comprising: one or more voltage inputs configured to generate logical control pulses within the pulse circuit, one or more high voltage power supplies configured to supply power to the pulse circuit, and a plurality of transistors, the plurality of transistors configured to drive the ultrasound transducer in response to dynamic currents generated at gates corresponding to one or more of the plurality of transistors.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
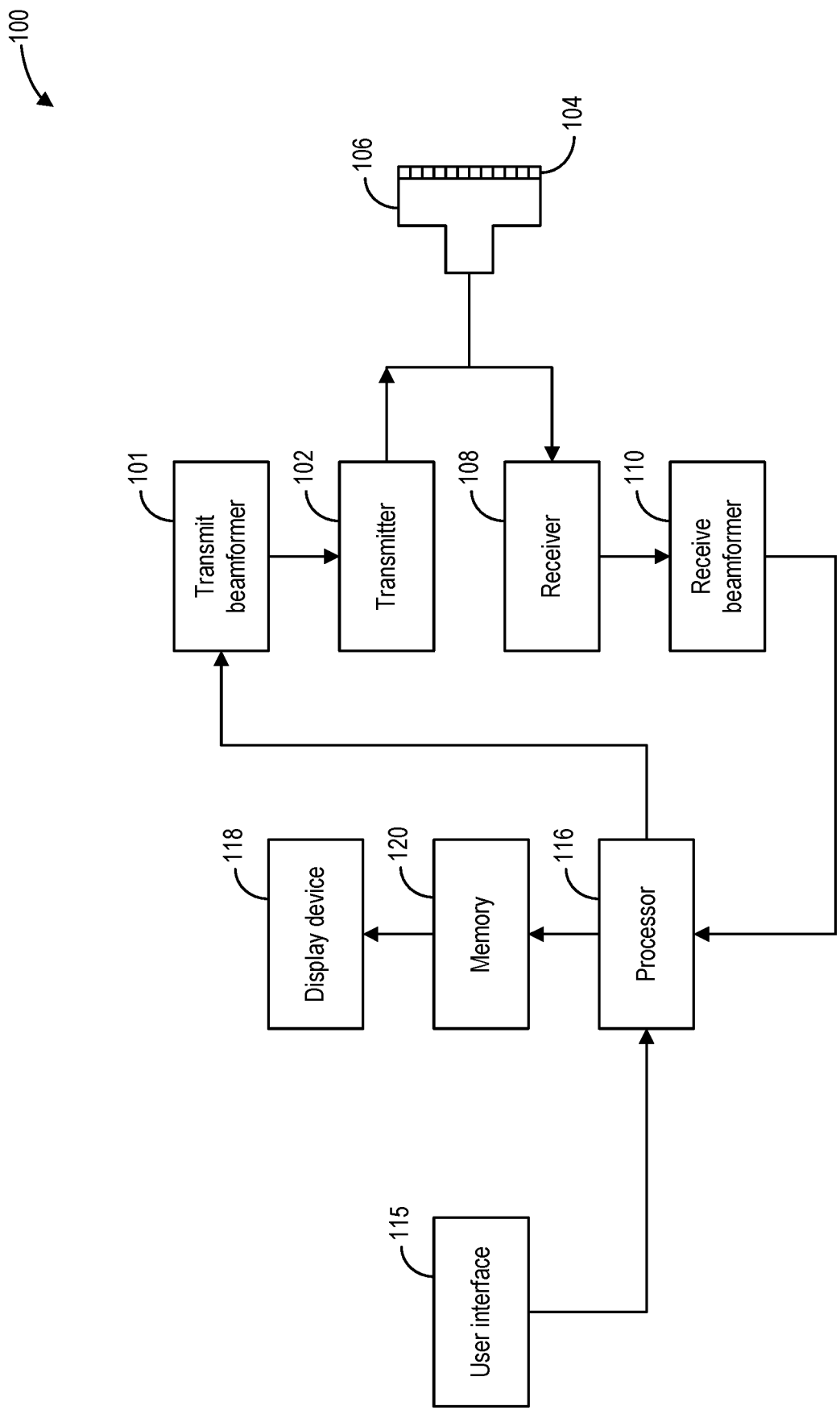
FIG. 1 shows a schematic example of an ultrasound system, according to an embodiment of the invention.

The following description relates to various embodiments of pulse circuits configured to convert one or more electrical pulses generated by an electrical waveform generator into acoustic ultrasonic pulses via a transducer of an ultrasound imaging system. Ultrasound transducers are included in an ultrasound imaging system, such as the ultrasound imaging system shown in FIG. 1. The ultrasound transducer may be electrically coupled to an electric waveform generator, whereby the electrical pulses generated therein may be amplified in order to allow the ultrasound transducer to be driven at high voltage. The amplification of a signal (e.g. an electrical waveform, such as spike pulses, square wave pulses, etc.) generated by the electric waveform generator may be actuated by a pulse circuit. A first schematic example of a pulse circuit is given in FIG. 2, which may be a two-level pulse circuit such as driven at two voltage levels. A pulse circuit may also be driven at more than two voltage levels as shown in a second schematic example of a three-level pulse circuit in FIG. 3. An example operation of a two-level pulse circuit is provided in an example prophetic graph, given in FIG. 4.

A pulse circuit may be configured to take as input one or more electrical pulses or logic control signals (e.g. as generated by an electrical waveform generator), and amplify them before an electrical output signal is used to drive the ultrasound transducer to produce acoustic pulses (herein referred to as transmit pulses). A pulse circuit may include one or more of a high voltage source, a high voltage reference circuit, and level shifting circuits. The high voltage reference circuit is a circuit electrically coupled to the high voltage source, which is able to maintain a reference voltage of the voltage source that might not fluctuate with parameters such as temperature or input current. A level shifter circuit is a circuit which may shift a voltage by a fixed amount. The reference voltage generated by the voltage reference circuit may then be used, in conjunction with the one or more level shifter circuits, to combine, amplify, and fix an amplitude of the input pulses in order to drive a gate of a transistor. The output of the transistor may then generate output voltage pulses to drive the ultrasound transducer at high voltage, such that the ultrasound transducer may generate the acoustic transmit pulses of sufficient amplitude. For example, an ultrasound transducer may have an operating voltage within the range of 10-250V.

However, a pulse circuit including one or more voltage reference circuits and one or more level shifter circuits may have potential drawbacks. For example, the high voltage reference circuits may operate by generating a static high voltage; generation of this static high voltage may contribute to increased power dissipation of the pulse circuit. The one or more voltage reference circuits may take up a large amount of area on a chip where the pulse circuit resides, adding to on-chip complexity. Further, the one or more voltage reference circuits may be sensitive to electrostatic discharge (ESD), potentially damaging the circuit. Additionally, the one or more level shifter circuits may operate by shifting logic control signals generated in the low voltage domain via static level shifting, which may also contribute to large power dissipation in the pulse circuit.

In one example, the aforementioned drawbacks may be alleviated by utilizing a pulse circuit that drives the ultrasound transducer via a dynamic current generated at the gate of the transistor, without the use of static voltage reference circuits or static level shifter circuits. The transistor may be driven via a dynamic switching mechanism, whereby a high voltage source may be dynamically, electrically coupled to the transistor, with the dynamic electrical coupling switched on and off as a function of the logic control signals. When the transistor is switched to be electrically coupled to the high voltage source, the high voltage source may dynamically drive a gate current of the transistor, which may allow the transistor to generate a high voltage output to drive the ultrasound transducer at high voltage.

In this way, by dynamically generating the output voltage driving the ultrasound transducer, power dissipation of the pulse circuit may be reduced. By eliminating the use of a static reference voltage circuit, ESD may be mitigated. Additionally, by removing level shifting and voltage reference sub-circuits with a pulse circuit architecture, circuit complexity may be reduced.

Turning now to FIG. 1, a schematic diagram of an ultrasound imaging system 100 in accordance with an embodiment of the invention is seen. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). The elements 104 of the probe may be made of ferroelectric materials, such as piezoelectric ceramic material such as PZT, PMN-PT, PZN-PT, and PIN-PMN-PT single crystal. According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer elements 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. The memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

Figure 2:
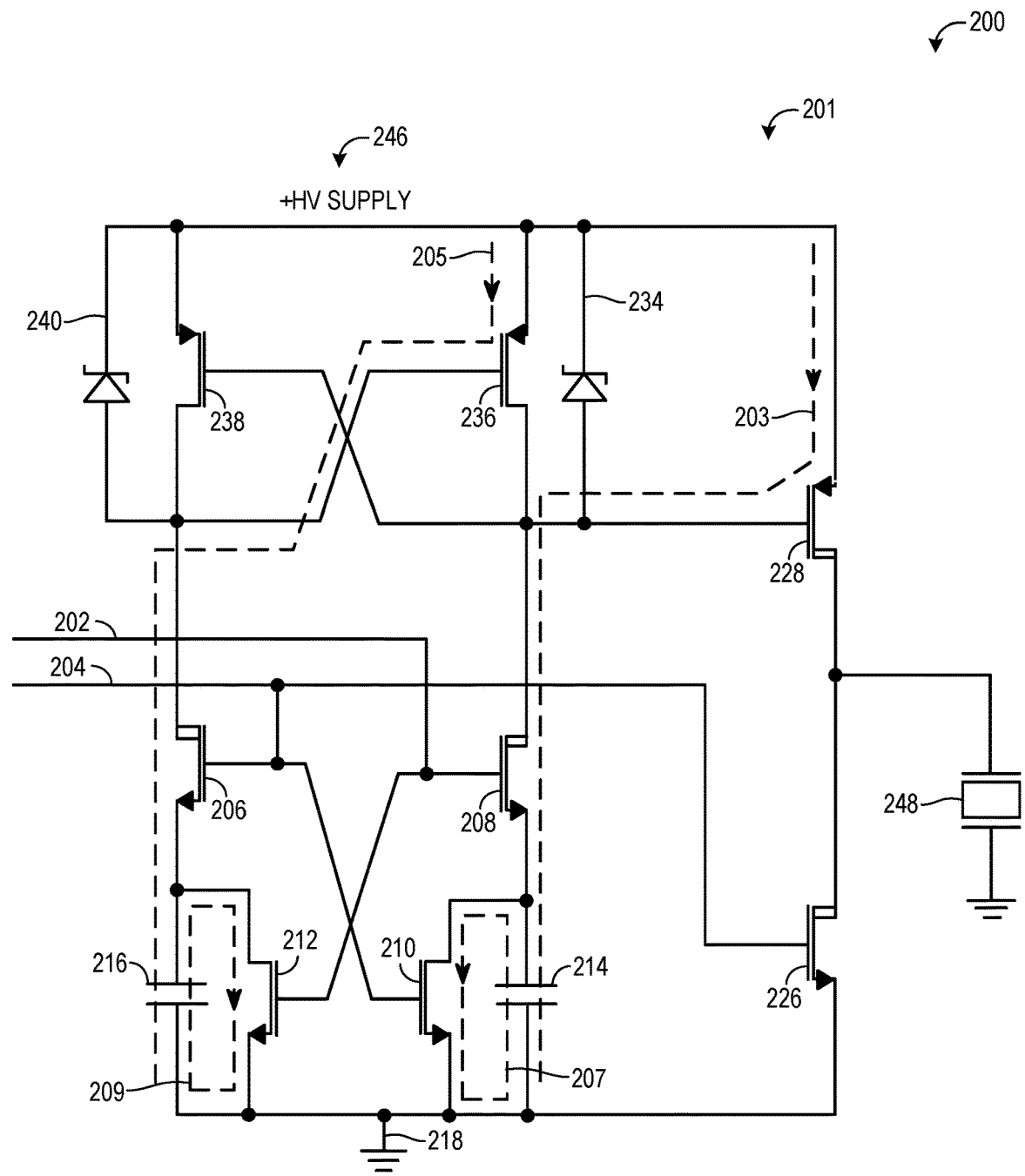
FIG. 2 shows a first schematic example of a two-level pulse circuit, according to an embodiment of the invention.

FIG. 2 shows a first embodiment 200 of a two-level pulse circuit 201, as part of a transmitter (such as transmitter 102 of FIG. 1) which may drive an ultrasound transducer 248 of an ultrasound imaging system (such as ultrasound imaging system 100 of FIG. 1). The ultrasound transducer 248 may be the same or significantly similar to one of the elements 104 of the transducer array 106 of FIG. 1. The pulse circuit 201 may be configured to receive logical control pulses at a positive voltage input 202 and an inverted positive voltage input 204 (e.g. the pulse generated from the positive voltage input 202 may be of positive voltage when the voltage at the inverted positive voltage input 204 is zero, and vice versa), and amplify the logical control pulses via a positive high voltage supply 246, in order to generate a high voltage output at the ultrasound transducer 248, which may then be converted into acoustic ultrasound pulses by the ultrasound transducer 248.

The positive high voltage supply 246 may be electrically coupled to each of a first source of a first transistor 236, a second source of a second transistor 238, a first cathode of a first Zener diode 234, and a second cathode of a second Zener diode 240. Each of the first transistor 236 and the second transistor 238 may be a field effect transistor (FET), for example a MOSFET or a JFET, among other example FETs, and may be rated for low source-drain voltages (e.g. voltages of up to +5V). A first gate of the first transistor 236 may be electrically coupled to a second drain of the second transistor 238, and a second gate of the second transistor 238 may be electrically coupled to a first drain of the first transistor 236. The first transistor 236 may have the first Zener diode 234 electrically coupled to each of the first source and the first drain of the first transistor 236, such that a cathode end of the first Zener diode 234 is electrically coupled to the first source of the first transistor 236, while an anode end of the first Zener diode 234 is electrically coupled to the first drain of the first transistor 236. Similarly, the second transistor 238 may have the second Zener diode 240 electrically coupled to each of the second source and the second drain of the second transistor 238, such that a cathode end of the second Zener diode 240 may be electrically coupled to the second source of the second transistor 238, and an anode end of the second Zener diode 240 may be electrically coupled to the second drain of the second transistor 238. Each of the first Zener diode 234 and the second Zener diode 240 may be configured to allow a voltage difference to be within a voltage limit between the sources and drains of the first transistor 236 and the second transistor 238, respectively.

Electrically coupled to each of the anode end of the second transistor 238, the first gate of the first transistor 236, and the anode end of the second Zener diode 240 is a fifth drain of a fifth transistor 206. The fifth transistor 206 may be a FET, may be rated for high source-drain voltages (e.g. beyond +5V), and may be for example a MOSFET or a JFET, among other example FETs. Similarly, a sixth transistor 208 may be electrically coupled to each of the anode end of the first Zener diode 234, the first drain of the first transistor 236, and the second gate of the second transistor 238. The sixth transistor 208 may be a field effect transistor (FET), may be rated for high source-drain voltages (e.g. voltages beyond +5V), and may be for example a MOSFET or a JFET, among other example FETs.

Coupled in series with the fifth transistor 206 is a seventh transistor 212. In other words, the fifth source of the fifth transistor 206 may be electrically coupled to a seventh drain of the seventh transistor 212. The seventh transistor 212 may be a FET, may be rated for low source-drain voltages (e.g. voltages up to +5V), and may be for example a MOSFET or a JFET, among other example FETs. Placed between a seventh source and the seventh drain of the seventh transistor 212 is a first capacitor 216, configured to charge and discharge as a voltage between the seventh source and the seventh drain of the seventh transistor 212 is altered. Similarly, coupled in series with the sixth transistor 208 is an eighth transistor 210. In other words, the sixth source of the sixth transistor 208 may be electrically coupled to an eighth drain of the eighth transistor 210. The eighth transistor 210 may be a FET, may be rated for low source-drain voltages (e.g. up to +5V), and may be for example a MOSFET or a JFET, among other example FETs. Placed between an eighth source and the eighth drain of the eighth transistor 210 is a second capacitor 214, configured to charge and discharge as a voltage between the eighth source and the eighth drain of the eighth transistor 210 is altered. The seventh source of the seventh transistor 212 and the eighth source of the eighth transistor 210 may be coupled to a ground 218.

Gates of the fifth transistor 206 and the eighth transistor 210 may be electrically coupled to each other, and may each be electrically coupled to the inverted positive voltage input 204, such that the inverted positive voltage input 204 may serve as an input for the gates of each of the fifth transistor 206 and the eighth transistor 210. Similarly, gates of the sixth transistor 208 and the seventh transistor 212 may be electrically coupled to each other, and may each be electrically coupled to the positive voltage input 202, such that the positive voltage input 202 may serve as an input for the gates of each of the sixth transistor 208 and the seventh transistor 212. In this way, the fifth transistor 206 and the eighth transistor 210 may be configured to switch on and off (e.g. allow or disallow source-drain voltages) based on a positive logical low-voltage signal generated by the inverted positive voltage input 204, while the sixth transistor 208 and the seventh transistor 212 may be configured to switch on and off based on a positive low-voltage signal generated by the positive voltage input 202.

Returning to the high voltage portion of the pulse circuit 201, including the high voltage supply 246, coupled to each of the cathode end and the anode end of the first Zener diode 234 is a third transistor 228. The third transistor 228 may be a FET, may be rated for high source-drain voltages (e.g. voltages beyond +5V), and may be for example a MOSFET or a JFET, among other example FETs. In particular, a third source of the third transistor 228 may be electrically coupled to the cathode end of the first Zener diode 234, while a third gate of the third transistor 228 may be coupled to an anode end of the first Zener diode. In this way, the first Zener diode 234 may be configured to significantly reduce a voltage difference between the third source and the third gate of the third transistor 228.

Electrically coupled in series with the third transistor 228 is a fourth transistor 226. In particular, the third drain of the third transistor 228 may be electrically coupled to a fourth drain of the fourth transistor 226. The fourth transistor 226 may be a FET, may be rated for high source-drain voltages (e.g. voltages beyond +5V), and may be for example a MOSFET or a JFET, among other example FETs. A fourth gate of the fourth transistor 226 may receive input from the inverted positive voltage input 204, and may thus be at the same voltage as the gates of each of the fifth transistor 206 and the eighth transistor 210. Further, the fourth source of the fourth transistor 226 may be electrically coupled to ground 218 via electrical coupling to second capacitor 214 and the eighth source of the eighth transistor 210.

Placed between the third drain of the third transistor 228 and the fourth drain of the fourth transistor 226 is the ultrasound transducer 248. The ultrasound transducer may be directly electrically coupled to and configured to be driven by a voltage between the third drain of the third transistor 228, and the fourth drain of the fourth transistor 226 at one end, while being coupled to ground at another end. The ultrasound transducer may emit one or more acoustic ultrasound pulses in response to the voltage between the third drain of the third transistor 228 and the fourth drain of the fourth transistor 226.

The pulse circuit 201 may operate in the following manner. The positive high voltage supply 246 may maintain a high voltage on each of the cathodes of the first and second Zener diodes, 234, 240, respectively, the sources of each of the first and second transistors 236, 238, respectively, and the third source of the third transistor 228.

Upon switching on of the pulse circuit 201, the positive voltage input 202 may send a positive voltage logical control pulse (e.g. may be any of a rectangular pulse, cosine squared pulse, Gaussian pulse, etc.), which may be received at gates of each of the sixth transistor 208 and the seventh transistor 212, respectively. Prior to generation of the positive voltage logical control pulse via the positive voltage input 202, the second capacitor 214 may be discharged (e.g. is storing no charge), while the first capacitor 216 may have a maximum charge. The voltage pulse received at the gates of each of the transistors 208, 212, may then switch on each of the transistors 208, 212. In particular, switching on of the seventh transistor 212 may allow a dynamic current between the seventh source and the seventh drain therein, allowing discharge of the first capacitor 216, as indicated by the dashed loop 209.

In contrast, switching on of the sixth transistor 208 may allow a first dynamic current to be generated from the third source of the third transistor 228, through the sixth drain and the sixth source of the sixth transistor 208, and to the second capacitor 214, the first dynamic current indicated by dashed line 203, thereby charging the second capacitor 214. The first dynamic current generated from the third source of the third transistor 228 may then generate a voltage between the third source and the third gate of transistor 228. This may allow the third transistor 228 to conduct current from the third source through the third drain, allowing a large voltage equal to the voltage of the positive high voltage supply 246 to be generated at the third drain of the third transistor 228, thereby providing a voltage equal to the voltage of the positive high voltage supply 246 to drive the ultrasound transducer 248, for the duration of the pulse (the pulse width) generated by the positive voltage input 202. The first Zener diode 234 may limit the resulting voltage across the third source and the third gate of the third transistor 228 to avoid break-down of the third transistor 228. Following completion of the positive voltage logical control pulse generated via the positive voltage input 202, the gates of each of the sixth transistor 208 and the seventh transistor 212 may be switched off, discontinuing current between the source and drain of the respective transistors.

In order to drive the ultrasound transducer 248 at a zero voltage, e.g. following driving of the ultrasound transducer 248 at high voltage via application of the positive voltage logical control pulse from positive voltage input 202, an inverted positive voltage logical control pulse may be generated (e.g. may be any of a rectangular pulse, cosine squared pulse, Gaussian pulse, etc.) via the inverted positive voltage input 204. The voltage pulse may be received at the gates of each of the fifth transistor 206 and the eighth transistor 210, switching on each of the transistors. In particular, switching on of the eighth transistor 210 may allow a dynamic current between the eighth source and the eighth drain therein, allowing discharge of the second capacitor 214, as indicated by the dashed loop 207.

In contrast, switching on of the fifth transistor 206 may allow a second dynamic current to be generated from the first gate of the first transistor 236, through the fifth drain and fifth source of the fifth transistor 206, and to the first capacitor 216, the second dynamic current indicated by dashed line 205, thereby charging the first capacitor. The second dynamic current 205 flowing from the first gate of the first transistor 236 may switch on the first transistor as the source-gate voltage of the first transistor increases to a bias voltage of the first transistor. Switching on of the first transistor may allow voltage equilibration for each of the third gate and third source of the third transistor 228, thereby switching off the third transistor.

Additionally, the voltage pulse generated by the inverted positive voltage input 204 may also be received at the fourth gate of the fourth transistor 226, switching on the fourth transistor. As the fourth source of the fourth transistor 226 is electrically coupled to the ground 218, the ultrasound transducer 248 may then be driven at ground. Further details of the operation of the pulse circuit 201 for driving the ultrasound transducer 248 are described in relation to FIG. 4.

In this way, the pulse circuit 201 may be utilized in a method to drive the ultrasound transducer 248, the method including switching on of the positive high voltage supply 246, the positive high voltage supply coupled to the third source of the third transistor 228, and sending a first positive voltage logical control pulse to the sixth gate of the sixth transistor 208, the first positive voltage logical control pulse generating a current between the sixth drain and sixth source of the sixth transistor. In response to the first positive voltage logical control pulse generating a current between the sixth drain and sixth source of the sixth transistor 208, the first dynamic current 203 may flow from the third gate of the third transistor 228 of the pulse circuit 201, the first dynamic current 203 switching on the third transistor 228, flowing through the sixth drain and the sixth source of the sixth transistor 208 to the second capacitor 214, and charging the second capacitor 214. Concomitantly with the charging of the second capacitor 214, the ultrasound transducer 284 coupled to the third drain of the third transistor 228 may then be driven at a first voltage of the third drain of the third transistor 228, the first voltage equal to a second voltage of the positive high voltage supply 246, with the first voltage generated in response to the switching on of the third transistor 228 via the first dynamic current 203. The driving of the ultrasound transducer 248 at the second voltage of the positive high voltage supply 246 may be activated in response to the third transistor 228 being switched on, the third transistor being switched on in response to the first dynamic current 203 charging the second capacitor 214 to a threshold level, the threshold level estimated based on a bias voltage of the third transistor.

Upon completion of generation of the first positive voltage logical control pulse, a second inverted positive voltage logical control pulse may be sent to each of the fourth gate of the fourth transistor 226 and the fifth gate of the fifth transistor 206 of the pulse circuit 201, where the second inverted positive voltage logical control pulse may generate a current between the fifth drain and the fifth source of the fifth transistor 206. In response to the second inverted positive voltage logical control pulse generating a current between the fifth drain and fifth source of the fifth transistor 206, the second dynamic current 205 may flow from the first gate of the first transistor 236 of the pulse circuit 201, where the second dynamic current may switch on the first transistor 236, and the second dynamic current may flow through the fifth drain and the fifth source of the fifth transistor to the first capacitor 216, and charging the first capacitor 216. Concomitantly with the charging of the first capacitor 216, the ultrasound transducer 248 coupled to the fourth drain of the fourth transistor 226 may be driven at a third voltage equal to ground via the fourth transistor, where the third voltage at the fourth transistor may be generated in response to the switching on of the fourth transistor 226 via second positive voltage logical control pulse received at the fourth gate of the fourth transistor 226. The driving of the ultrasound transducer 248 at ground via the fourth transistor 226 may be initiated by the second inverted positive voltage logical control pulse being received at the fourth gate of the fourth transistor 226 and following switching off of the third transistor 228, the third transistor 228 being switched off in response to the first transistor 236 being switched on, where the first transistor 236 is switched on in response to the second dynamic current 205 charging the first capacitor 216 to a threshold level, the threshold level is determined by a bias voltage of the first transistor 236.

By utilizing the pulse circuit 201 configured to generate high voltages at the transducer 248 via dynamic currents, the use of components that generate high, static voltages and which consume large amounts of power, such as state level shifters and static voltage reference circuits, may be avoided, and energy efficiency may be increased for the ultrasound system.

Figure 3:
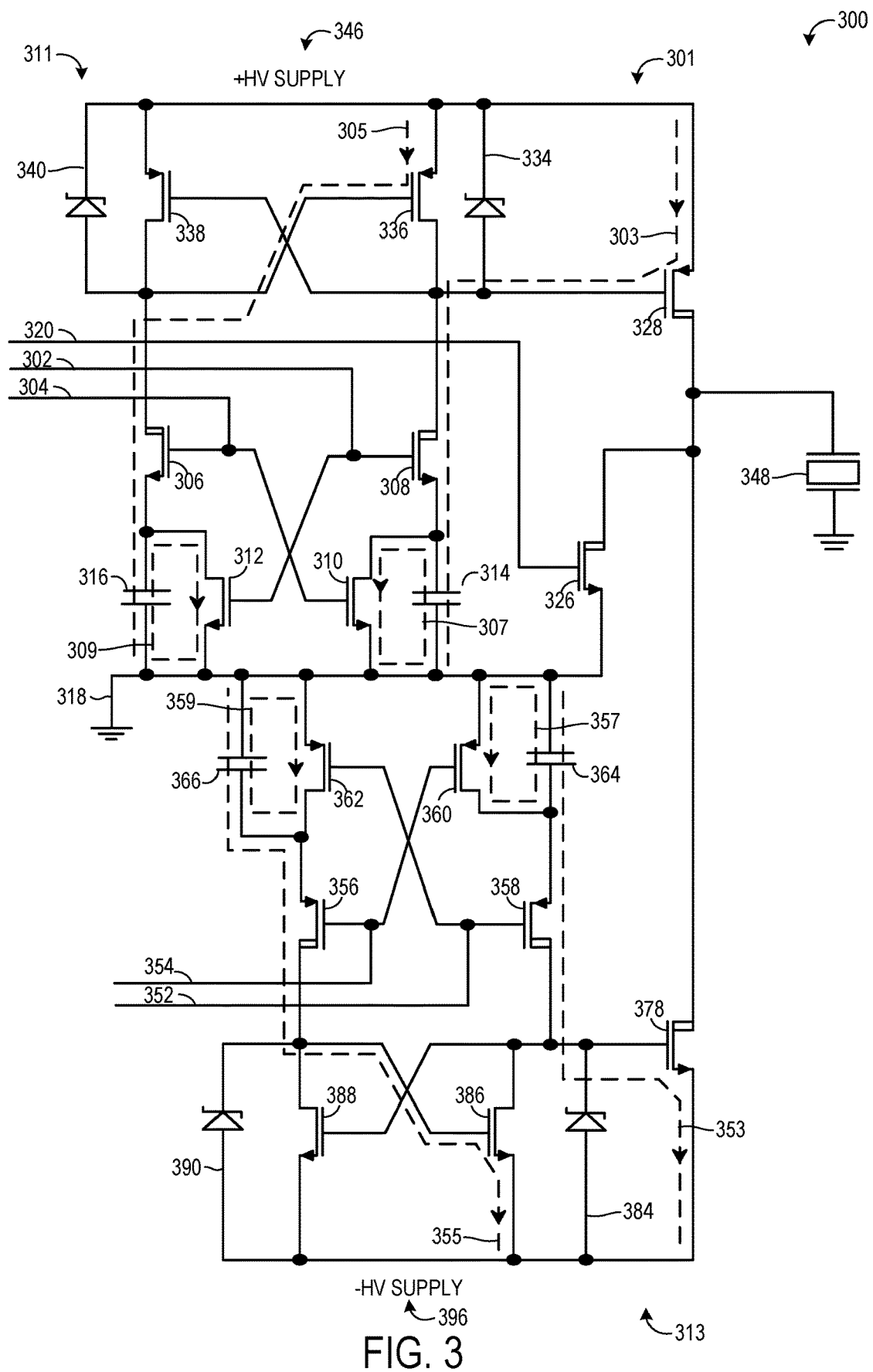
FIG. 3 shows a second schematic example of a three-level pulse circuit, according to an embodiment of the invention.

FIG. 3 shows a second embodiment 300 of a three-level pulse circuit 301, as part of a transmitter (such as transmitter 102 of FIG. 1) which may drive an ultrasound transducer 348 of an ultrasound imaging system (such as ultrasound imaging system 100 of FIG. 1). The ultrasound transducer 348 may be the same or significantly similar to one of the elements 104 of the transducer array 106 of FIG. 1. In contrast to the pulse circuit 201 of FIG. 2, the three-level pulse circuit 301 may include a positive high voltage circuit 311 configured to drive the ultrasound transducer 348 at a high positive voltage, the positive high voltage circuit 311 driven by a positive high voltage supply 346, and a negative high voltage circuit 313 configured to drive the ultrasound transducer 348 at a high negative voltage, the negative high voltage circuit 313 driven by a negative high voltage supply 396. It will be appreciated that components of the positive high voltage circuit 311 are substantially similar to or identical to components of the pulse circuit 201 of FIG. 2, and may be labeled with corresponding numbers, prefixed with a "3" instead of a "2". For example, the first transistor 336 may be substantially similar to or identical to the first transistor 236.

The positive high voltage circuit 311 may be configured to receive logical control pulses at a first positive voltage input 302 and a second inverted positive voltage input 304, and amplify the logical control pulses via the positive high voltage supply 346, in order to generate a high positive voltage output at the ultrasound transducer 348, which may then be converted into acoustic ultrasound pulses by the ultrasound transducer 348.

Similarly, the negative high voltage circuit 313 may be configured to receive logical control pulses at a fourth positive voltage input 352 and a fifth inverted positive voltage input 354, and amplify the logical control pulses via the negative high voltage supply 396, in order to generate a high negative voltage output at the ultrasound transducer 348, which may then be converted into acoustic ultrasound pulses by the ultrasound transducer 348.

The negative high voltage circuit 313 may be a mirror reflection of the positive high voltage circuit 311, mirrored about a horizontal axis defined by a ground line 318, such that both the positive high voltage circuit 311 and the negative high voltage circuit 313 are coupled to the ground line 318. In this way, the components of the positive high voltage circuit 311 are substantially similar to or identical to the "mirrored" components of the negative high voltage circuit 313. In particular, a seventh and an eighth Zener diode 384, 390 may be the same or significantly similar to the first and second Zener diodes 334, 340, respectively, a thirteenth, fourteenth, fifteenth, and a sixteenth transistor 356, 358, 362, 360 may be the same or significantly similar to the first, second, third, and eighth transistors 306, 308, 312, 310, respectively, a third and fourth capacitor 366, 364, may be the same or significantly similar to the first and second capacitors 316, 314, respectively, a fourth positive voltage input 352 may be the same or significantly similar to the first positive voltage input 302, a fifth inverted positive voltage input 354 may be the same or significantly similar to the second inverted positive voltage input 304. However, in contrast to the positive high voltage circuit 311, there might not be a transistor in the negative high voltage circuit 313 that corresponds to the fourth transistor 326. Additionally, in contrast to the pulse circuit 201 of FIG. 2, the fourth transistor 326 of positive high voltage circuit 311 might not be electrically coupled to the second inverted positive voltage input 304, and may instead be coupled to a third positive voltage input 320 via a fourth gate of the fourth transistor 326, the third positive voltage input 320 configured to generate logical control pulses (e.g. may be any of a rectangular pulse, cosine squared pulse, Gaussian pulse, etc.) in order to switch on and off the fourth transistor 326. Further, while the first, second and third transistors 336, 338, 328, of the positive high voltage circuit 311 may switch on with a positive source-gate voltage (e.g. p-channel operation), the ninth, tenth, and eleventh transistors 386, 388, 378, of the negative high voltage circuit 313 may switch on with a negative source-gate voltage (e.g. n-channel operation).

The positive high voltage circuit 311 may operate in a substantially similar as the pulse circuit 201 of FIG. 2, as described in relation to FIG. 2, whereby a first dynamic current 303 may cause the third transistor 328 to drive the ultrasound transducer 348, and a second dynamic current 305 may switch off driving of the ultrasound transducer 348 by the third transistor 328, the first dynamic current 303 and the second dynamic current 305 generated in response to control pulses via the first positive voltage input 302 and the second inverted positive voltage input 304, respectively. However, in contrast to the pulse circuit 201 of FIG. 2, the fourth transistor 326 may be switched on and off via the third positive voltage input 320, the third positive voltage input 320 controlled independently of each of the first positive voltage input 302 and the second inverted positive voltage input 304.

Similarly, the negative high voltage circuit 313 may operate in a similar, "mirrored" manner to the positive high voltage circuit 311, in which the fourth positive voltage input 352 is configured to generate a positive voltage logical control pulse (e.g. may be any of a rectangular pulse, cosine squared pulse, Gaussian pulse, etc.), which may be received at gates of the fourteenth transistor 358 and the fifteenth transistor 362. Upon receiving the positive voltage logical control pulse, the transistors 358, 362 may be switched on, allowing discharge of the third capacitor 366, as indicated by the dashed loop 359, and allowing generation of a third dynamic current to be generated from an eleventh gate of the eleventh transistor 378, through a fourteenth drain and a fourteenth source of the fourteenth transistor 358, and to the fourth capacitor 364, the third dynamic current indicated by dashed line 353, thereby charging the fourth capacitor.

The third dynamic current generated from the eleventh gate of the eleventh transistor 378 may then generate a voltage between the eleventh source and the eleventh gate of the eleventh transistor 378, allowing a large voltage equal to the voltage of the negative high voltage supply 396 to be generated at the eleventh drain of the eleventh transistor 378, thereby providing a voltage equal to the voltage of the negative high voltage supply 396 to drive the ultrasound transducer 348, for the duration of the pulse (the pulse width) generated by the fourth positive voltage input 352. Following completion of the positive voltage logical control pulse generated via the fourth positive voltage input 352, gates of each of the fourteenth transistor 358 and the fifteenth transistor 362 may be switched off, discontinuing current between sources and drains of the respective transistors.

The fifth inverted positive voltage input 354 may be used to switch off driving of the ultrasound transducer 348 at high negative voltage via the eleventh transistor 378, e.g. following driving of the ultrasound transducer 348 at high negative voltage via application of the positive voltage logical control pulse from the fourth positive voltage input 352. A second, inverted positive voltage logical control pulse may be generated (e.g. may be any of a rectangular pulse, cosine squared pulse, Gaussian pulse, etc.) via the fifth inverted positive voltage input 354. The voltage pulse may be received at gates of each of the thirteenth transistor 356 and the sixteenth transistor 360, switching on each of the transistors. In particular, switching on of the sixteenth transistor 360 may allow a dynamic current between a sixteenth source and a sixteenth drain therein, allowing discharge of the fourth capacitor 364, as indicated by the dashed loop 357.

In contrast, switching on of the thirteenth transistor 356 may allow a fourth dynamic current to be generated from a ninth gate of the ninth transistor 386, through a thirteenth drain and a thirteenth source of the thirteenth transistor 356, and to the third capacitor 366, the fourth dynamic current indicated by dashed line 355, thereby charging the third capacitor. The fourth dynamic current 355 flowing from the ninth gate of the ninth transistor 386 may switch on the ninth transistor as the source-gate voltage of the ninth transistor increases in magnitude to a bias voltage of the ninth transistor. Switching on of the ninth transistor 386 may allow voltage equilibration for each of an eleventh gate and an eleventh source of the eleventh transistor 378, thereby switching off the eleventh transistor.

The logical control pulses generated by each of the first positive voltage input 302, the second inverted positive voltage input 304, the third positive voltage input 320, the fourth positive voltage input 352, and the fifth inverted positive voltage input 354 may be generated in several combinations. In one example, an example logical control pulse sequence may be generation of a first logical control pulse by the first positive voltage input 302, a second logical control pulse generated by the second inverted positive voltage input 304 in coordination (e.g. at a significantly similar time) with a third logical control pulse generated by the third positive voltage input 320, a fourth logical control pulse generated by the fourth positive voltage input 352, and a fifth logical control pulse generated by the fifth inverted positive voltage input 354 in coordination (e.g. at a significantly similar time) with a sixth logical control pulse generated by the third positive voltage input 320, thereby driving the ultrasound transducer 348 at a high positive voltage pulse, followed by a ground voltage pulse, followed by a high negative voltage pulse, followed by a ground voltage pulse, respectively. However, the above example control sequence should be understood as a non-limiting example, and other example control sequences may be carried out.

Figure 4:
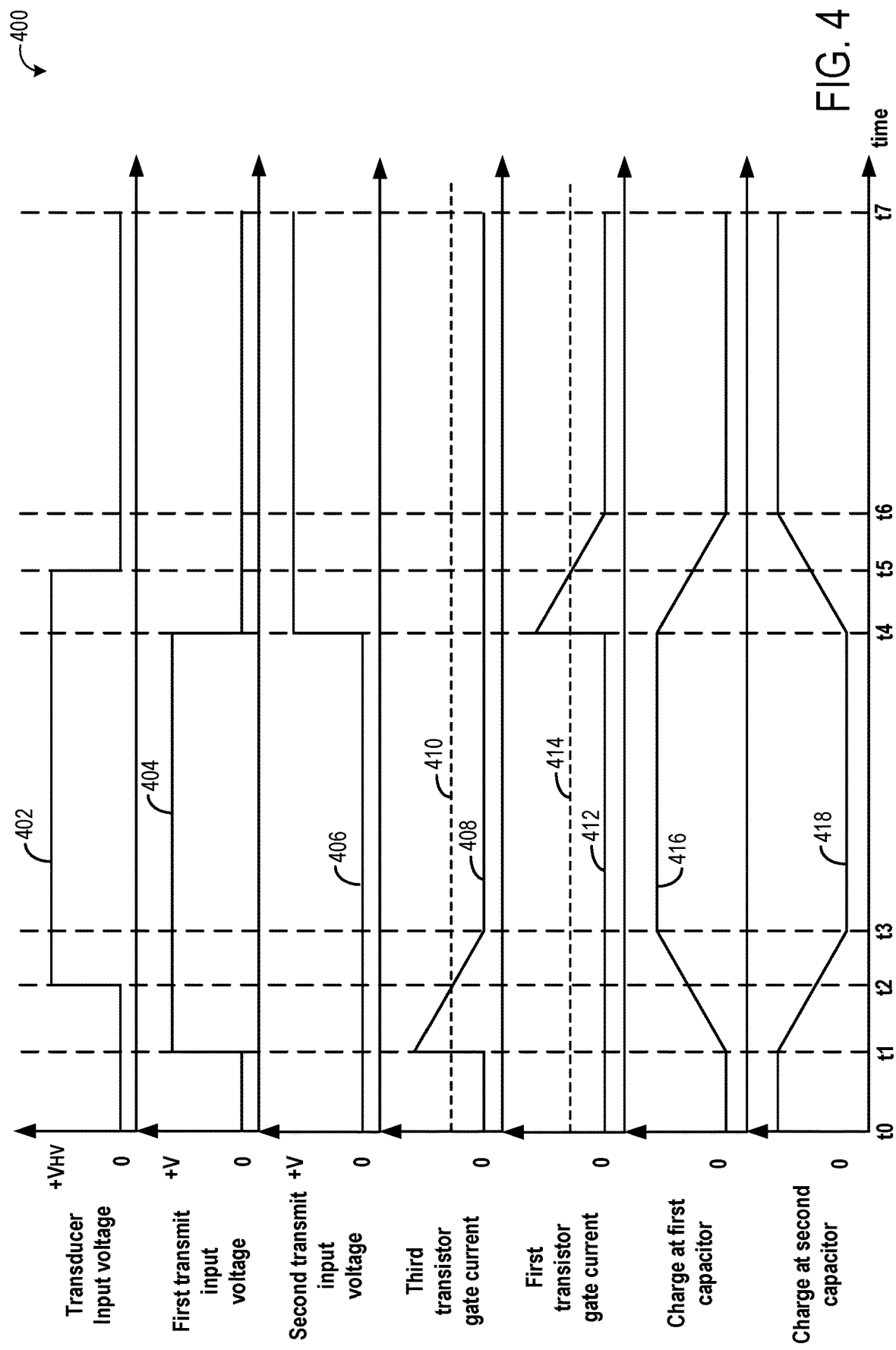
FIG. 4 shows an example timeline of operation of the first schematic example of FIG. 2 of the pulse circuit, according to the present disclosure.

FIG. 4 shows an example timeline 400 of operation of a pulse circuit (such as pulse circuit 201 of FIG. 2) for an ultrasound transducer (such as ultrasound transducer 248 of FIG. 2). The horizontal (x-axis) denotes time, and the vertical markers t0-t7 identify significant times during the operation of the pulse circuit.

The example timeline 400 shows operation of the pulse circuit, whereby a positive voltage source (such as positive high voltage supply 246 of FIG. 2) may be utilized within the pulse circuit to amplify logical control pulses generated by a waveform generator, the logical control pulses received as input to the pulse circuit via each of a positive voltage input (e.g. positive voltage input 202) and an inverted positive voltage input (e.g. inverted positive voltage input 204). The amplified output voltage of the pulse circuit may then be utilized to drive the ultrasound transducer, whereby the amplified voltage at the input of the ultrasound transducer may be converted into an acoustic pulse via the ultrasound transducer. The ultrasound transducer input voltage is shown in plot 402. The logical control signals (e.g. transmit signals) generated by each of the positive voltage input and the inverted positive voltage input are shown in plots 404 and 406, respectively.

In order to generate a large positive voltage at the ultrasound transducer, the pulse circuit may generate a first dynamic current within the pulse circuit at a third gate of a third transistor (e.g. third transistor 228). The first dynamic current is generated in response to an application of a positive voltage logical control pulse via the positive voltage input; the dynamic current generated at the third gate of third transistor is shown in plot 408. The third transistor may then be switched on as the source-gate voltage increases to the bias voltage of the third transistor; the bias voltage of the third transistor is shown as dashed line 410.

Similarly, in order to switch off driving of the ultrasound transducer by the third transistor, a second dynamic current may be generated at a first gate of a first transistor (e.g. first transistor 236) in response to application of a second positive voltage logical control pulse via the inverted positive voltage input. The second dynamic current is shown in plot 412 of the first transistor gate current. The first transistor may then be switched on as the source-gate voltage increases to the bias voltage of the first transistor; the bias voltage of the first transistor is shown as dashed line 414. Each of the first dynamic current and the second dynamic current flow to a first capacitor and a second capacitor (e.g. first capacitor 216 and second capacitor 214), respectively. The charge at the first capacitor is shown in plot 416, and the charge at the second capacitor is shown in plot 418.

At time t0, the pulse circuit is on, (the positive high voltage supply is on at a voltage of $+V_{HV}$), but no input is generated at either of the positive voltage input or the inverted positive voltage input. Correspondingly, the first transmit input voltage is zero, the second transmit input voltage is zero, the gate current at the third transistor is zero, the gate current at the first transistor is zero. The first capacitor is initialized in a discharged state (no charge stored at the first capacitor), while the second capacitor is initialized in a charged state (the second capacitor is charged).

At time t1, a first positive voltage logical control signal is generated at the positive voltage input, as part of generating a positive high voltage at the input of the ultrasound transducer in order to drive the ultrasound transducer, thereby generating an acoustic ultrasound pulse. Consequently, the first transmit input voltage is at a voltage +V; the second transmit input voltage remains at 0. The first transmit input voltage is received at gates of each of a sixth transistor (e.g. 208) and a seventh transistor (e.g. 212), switching on each of the sixth transistor and the seventh transistor. In response, a first dynamic current (e.g. 203) is generated at the third gate of the third transistor, first flowing from the positive high voltage supply into a third source of the third transistor, and leaving the third gate of the of the third transistor. The first dynamic current then flows through a sixth drain and a sixth source of the sixth transistor, and into the first capacitor, thereby charging the first capacitor. Simultaneously, due to the switching on of the seventh transistor, the second capacitor is discharged as a current leaving the second capacitor cycles through a seventh drain and a seventh source of the seventh transistor.

Consequently, from t1 to t3, in response to the constant first transmit input voltage at +V, and as the first dynamic current flows from the third gate of the third transistor to the first capacitor, the charge at the first capacitor ramps up from 0 to a maximum value, and the charge at the second capacitor decays from a maximum value to 0.

At t2, as the first dynamic current flowing from the gate of the third transistor continues to decrease, the corresponding source-gate voltage of the third transistor increases to the bias voltage of the third gate; in response, the third transistor switches from an off position to an on position, causing the transducer input voltage to switch from 0 to $+V_{HV}$.

From t2 to t3, the transducer input voltage continues to be maintained at $+V_{HV}$. The third transistor gate current continues to decrease, and correspondingly the charge at the first capacitor continues to increase. Concurrently, the charge from the second capacitor continues to be discharged.

At t3, the first capacitor is fully charged, the second capacitor is fully drained, and the transducer input voltage is at its maximum valve $+V_{HV}$. From t3 to t4, the transmit input voltage is maintained at +V for the remainder of the voltage pulse, and in response, the transducer input voltage is maintained at $+V_{HV}$. Correspondingly, the charge at the first capacitor is maintained at its maximum value, while the charge at the second capacitor is maintained at 0.

At t4, the first transmit input voltage switches from +V to 0, while the second transmit input voltage switches from 0 to +V. The second transmit pulse is then received at gates of each of a fifth transistor (e.g. 206), an eighth transistor (e.g. 210), and a fourth transistor (e.g. 226). In response to the beginning of the second transmit pulse, each of the fifth transistor, the eighth transistor, and the fourth transistor is switched on. Switching on of the eighth transistor allows for the first capacitor to be discharged, while switching on of the fifth transistor allows for generation of a second dynamic current (e.g. 205) generated at a first gate of the first transistor, first flowing from the positive high voltage supply to a first source of the first transistor, and leaving the first gate of the first transistor. The second dynamic current then flows through a fifth drain and a fifth source of the fifth transistor, and into the second capacitor, thereby charging the second capacitor. Simultaneously, due to the switching on of the eighth transistor, the first capacitor is discharged as a current leaving the first capacitor cycles through an eighth drain and an eighth source of the eighth transistor.

Consequently, from t4 to t6, in response to the constant second transmit input voltage at +V, and as the current flows from the first gate of the first transistor to the second capacitor, the charge at the second capacitor ramps up from 0 to a maximum value, and the charge at the first capacitor decays from a maximum value to 0.

At t5, as the gate current from the first transistor continues to decrease, the corresponding source-gate voltage of the first transistor increases to the bias voltage of the first gate; in response, the first transistor switches from an off position to an on position. Due to the first transistor switching from an off position to an on position, the voltage of each of the third gate and the third source of the third transistor are equilibrated, thereby switching off the third transistor. Switching off of the third transistor, in conjunction with the fourth transistor switching to an on state from t4, causes the transducer input voltage to switch from $+V_{HV}$ to 0.

From t5 to t6, the transducer input voltage continues to be maintained at 0. The first transistor gate current continues to decrease, and correspondingly the charge at the second capacitor continues to increase. Concurrently, the charge from the first capacitor continues to be discharged.

At t6, the second capacitor is fully charged, the first capacitor is fully drained, and the transducer input voltage is at 0. From t6 to t7, the transmit input voltage is maintained at +V for the remainder of the voltage pulse, and in response, the transducer input voltage is maintained at 0. Correspondingly, the charge at the second capacitor is maintained at its maximum value, while the charge at the second capacitor is maintained at 0. At t7, the method ends.

In this way, a pulse circuit may be part of an ultrasound system, the ultrasound system comprising an ultrasound transducer configured to generate acoustic ultrasonic pulses in response to electronic driving, and a pulse circuit electrically coupled to and configured to drive the ultrasound transducer. The pulse circuit may further comprise one or more voltage inputs configured to generate logical control pulses within the pulse circuit, and one or more high voltage power supplies configured to supply power to the pulse circuit. The pulse circuit may also include a plurality of transistors, the plurality of transistors configured to drive the ultrasound transducer in response to dynamic currents generated at gates corresponding to one or more of the plurality of transistors, and a first diode included between a first source and a first drain of a first transistor and a second diode included between a second source and a second drain of a second transistor.

By utilizing dynamical charging and discharging from the gates of transistors in the pulse circuit of the ultrasound system, the use of static voltage level shifters and a static high voltage reference sub-circuit may be avoided. The technical effect of eliminating static voltage level shifters and the high voltage reference sub-circuit from the pulse circuit is that power dissipation that is a consequence of maintaining constant static voltages may be reduced. In removing the high voltage reference sub-circuit, the resulting pulse circuit may take up less area on a chip, leading to greater chip design efficiency. Further, removal of the high voltage reference sub-circuit may reduce the possibility of electrostatic discharge (ESD), which may damage the pulse circuit. Overall, by utilizing dynamic currents to switch on and off transistors within the pulse circuit, the ultrasound transducer may be driven in a more energy efficient manner and with faster response times as compared to a pulse circuit utilizing static voltage level shifters and the high voltage reference sub-circuit.

The disclosure provides support for an ultrasound system comprising: an ultrasound transducer configured to generate acoustic ultrasonic pulses in response to electronic driving, a pulse circuit electrically coupled to and configured to drive the ultrasound transducer, the pulse circuit further comprising: one or more voltage inputs configured to generate logical control pulses within the pulse circuit, one or more high voltage power supplies configured to supply power to the pulse circuit, and a plurality of transistors, the plurality of transistors configured to drive the ultrasound transducer in response to dynamic currents generated at gates corresponding to one or more of the plurality of transistors. In a first example of the system, the system further comprises: a first Zener diode included between a first source and a first drain of a first transistor and a second Zener diode included between a second source and a second drain of a second transistor, wherein the first Zener diode is configured to limit a voltage across the first transistor, and wherein the second Zener diode is configured to limit another voltage across the second transistor. In a second example of the system, optionally including the first example, the one or more high voltage power supplies includes a first positive high voltage power supply directly electrically coupled to each of the first drain of the first transistor, a first cathode of the first Zener diode, the second drain of the second transistor, and a second cathode of the second Zener diode. In a third example of the system, optionally including one or both of the first and second examples, the plurality of transistors includes the first transistor, the second transistor, a third transistor, and a fourth transistor, and wherein a first gate of the first transistor is directly electrically coupled to each of the second drain of the second transistor and a second anode of the second Zener diode, a second gate of the second transistor is directly coupled to each of the first drain of the first transistor and a first anode of the first Zener diode, a third gate of the third transistor is directly electrically coupled to the first anode of the first Zener diode, and a fourth gate of the fourth transistor is directly electrically coupled to a second positive input voltage of the one or more voltage inputs. In a fourth example of the system, optionally including one or more or each of the first through third examples, the system further comprises: each of a fifth transistor, a sixth transistor, a seventh transistor, and an eighth transistor, wherein a fifth gate of the fifth transistor is directly electrically coupled to an eighth gate of the eighth transistor, wherein a fifth source of the fifth transistor is directly electrically coupled to a seventh drain of the seventh transistor, and wherein a fifth drain of the fifth transistor is directly electrically coupled to each of the second anode of the second Zener diode and the second drain of the second transistor. In a fifth example of the system, optionally including one or more or each of the first through fourth examples, a sixth gate of the sixth transistor is directly electrically coupled to a seventh gate of the seventh transistor, wherein a sixth source of the sixth transistor is directly electrically coupled to the seventh drain of the seventh transistor, and wherein a sixth drain of the sixth transistor is electrically directly coupled to each of a third drain of the third transistor of the plurality of transistors, the first anode of the first Zener diode, and the third gate of the third transistor. In a sixth example of the system, optionally including one or more or each of the first through fifth examples, the seventh gate of the seventh transistor is directly electrically coupled to the sixth gate of the sixth transistor, wherein the seventh drain of the seventh transistor is directly electrically coupled to the sixth source of the sixth transistor and a first end of a first capacitor, and wherein a seventh source of the seventh transistor is directly electrically coupled to a ground line and a second end of the first capacitor. In a seventh example of the system, optionally including one or more or each of the first through sixth examples, the eighth gate of the eighth transistor is directly electrically coupled to the fifth gate of the fifth transistor, and wherein an eighth drain of the eighth transistor is directly electrically coupled to the sixth source of the sixth transistor and a first end of a second capacitor, and wherein the seventh source of the seventh transistor is directly electrically coupled to a ground line and a second end of the second capacitor. In an eighth example of the system, optionally including one or more or each of the first through seventh examples, the one or more voltage inputs includes a positive voltage input configured to send a positive voltage logical control pulse to gates of each of the fifth transistor and the eighth transistor, and an inverted positive voltage input configured to send a second positive voltage logical control pulse to gates of each of the sixth transistor, the seventh transistor, and the fourth transistor. In a ninth example of the system, optionally including one or more or each of the first through eighth examples, the pulse circuit is a three-level pulse circuit, including a positive high voltage circuit and a negative high voltage circuit, the positive high voltage circuit electrically coupled to and configured to drive the ultrasound transducer at positive high voltage, and the negative high voltage circuit electrically coupled to and configured to drive the ultrasound transducer at negative high voltage, and wherein the positive high voltage circuit includes a second positive high voltage power supply of the one or more high voltage power supplies, the second positive high voltage power supply configured to supply power to the positive high voltage circuit, and wherein the negative high voltage circuit includes a third negative high voltage power supply of the one or more high voltage power supplies, the third negative high voltage power supply configured to supply power to the negative high voltage circuit. In a tenth example of the system, optionally including one or more or each of the first through ninth examples, the system further comprises: a fourth source of the fourth transistor, the fourth source directly electrically coupled to the second end of the first capacitor, the second end of the first capacitor directly electrically coupled to the ground line. In an eleventh example of the system, optionally including one or more or each of the first through tenth examples, an input of the ultrasound transducer is directly electrically coupled to each of a third drain of the third transistor and a fourth drain of the fourth transistor.

The disclosure also provides support for a method for a pulse circuit coupled to an ultrasound transducer of an ultrasound system, the method comprising: switching on a positive high voltage supply of the pulse circuit, the positive high voltage supply coupled to a third source of a third transistor, sending a first positive voltage logical control pulse to a sixth gate of a sixth transistor of the pulse circuit, the first positive voltage logical control pulse generating a current between a sixth drain and sixth source of the sixth transistor, flowing a first dynamic current from a third gate of the third transistor of the pulse circuit, the first dynamic current switching on the third transistor, the first dynamic current flowing through the sixth drain and the sixth source of the sixth transistor to a first capacitor, and charging the first capacitor, and driving the ultrasound transducer coupled to a third drain of the third transistor at a first voltage of the third drain of the third transistor, the first voltage equal to a second voltage of the positive high voltage supply, the first voltage generated in response to the switching on of the third transistor via the first dynamic current. In a first example of the method, the method further comprises: sending the first positive voltage logical control pulse to a seventh gate of a seventh transistor of the pulse circuit, and allowing discharge of a second capacitor placed between a seventh source and a seventh drain of the seventh transistor. In a second example of the method, optionally including the first example, driving of the ultrasound transducer at the second voltage of the positive high voltage supply is activated in response to the third transistor being switched on, wherein the third transistor being switched on in response to the first dynamic current charging the first capacitor to a threshold level, the threshold level estimated based on a bias voltage of the third transistor. In a third example of the method, optionally including one or both of the first and second examples, the method further comprises: upon completion of generation of the first positive voltage logical control pulse, sending a second inverted positive voltage logical control pulse to each of a fourth gate of a fourth transistor and a fifth gate of a fifth transistor of the pulse circuit, the second inverted positive voltage logical control pulse generating a current between a fifth drain and a fifth source of the fifth transistor, flowing a second dynamic current from a first gate of a first transistor of the pulse circuit, the second dynamic current switching on the first transistor, the second dynamic current flowing through the fifth drain and the fifth source of the fifth transistor to the second capacitor, and charging the second capacitor, and driving the ultrasound transducer coupled to a fourth drain of the fourth transistor at a third voltage equal to ground via the fourth transistor, the third voltage at the fourth transistor generated in response to the switching on of the fourth transistor via second positive voltage logical control pulse received at the fourth gate of the fourth transistor. In a fourth example of the method, optionally including one or more or each of the first through third examples, the method further comprises: sending the second inverted positive voltage logical control pulse to an eighth gate of an eighth transistor of the pulse circuit, allowing discharge of the first capacitor placed between an eighth source and an eighth drain of the eighth transistor. In a fifth example of the method, optionally including one or more or each of the first through fourth examples, driving of the ultrasound transducer at ground via the fourth transistor is initiated by the second inverted positive voltage logical control pulse being received at the fourth gate of the fourth transistor and following switching off of the third transistor, the third transistor being switched off in response to the first transistor being switched on, the first transistor being switched on in response to the second dynamic current charging the second capacitor to a threshold level, and wherein the threshold level is determined by a bias voltage of the first transistor.

The disclosure also provides support for an ultrasound system comprising: an ultrasound transducer configured to generate acoustic ultrasonic pulses in response to electronic driving, a pulse circuit electrically coupled to and configured to drive the ultrasound transducer, the pulse circuit further comprising: one or more voltage inputs configured to generate logical control pulses within the pulse circuit, one or more high voltage power supplies configured to supply power to the pulse circuit, a plurality of transistors, the plurality of transistors configured to drive the ultrasound transducer in response to dynamic currents generated at gates corresponding to one or more of the plurality of transistors, and a first diode included between a first source and a first drain of a first transistor and a second diode included between a second source and a second drain of a second transistor. In a first example of the system, the pulse circuit is a three-level pulse circuit, including a positive high voltage circuit and a negative high voltage circuit, the positive high voltage circuit electrically coupled to and configured to drive the ultrasound transducer at positive high voltage, and the negative high voltage circuit electrically coupled to and configured to drive the ultrasound transducer at negative high voltage.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound system comprising:
   an ultrasound transducer configured to generate acoustic ultrasonic pulses in response to electronic driving;
   a pulse circuit electrically coupled to and configured to drive the ultrasound transducer, the pulse circuit further comprising:
   one or more voltage inputs configured to generate logical control pulses within the pulse circuit;
   one or more high voltage power supplies configured to supply power to the pulse circuit; and
   a plurality of transistors, the plurality of transistors configured to drive the ultrasound transducer in response to dynamic currents generated at gates corresponding to one or more of the plurality of transistors,
   wherein the pulse circuit is a three-level pulse circuit, including a positive high voltage circuit and a negative high voltage circuit, both the positive high voltage circuit and the negative high voltage circuit configured to drive the ultrasound transducer.

2. The ultrasound system of claim 1, further comprising a first Zener diode included between a first source and a first drain of a first transistor and a second Zener diode included between a second source and a second drain of a second transistor, wherein the first Zener diode is configured to limit a voltage across the first transistor, and wherein the second Zener diode is configured to limit another voltage across the second transistor.

3. The ultrasound system of claim 2, wherein the one or more high voltage power supplies includes a first positive high voltage power supply directly electrically coupled to each of the first drain of the first transistor, a first cathode of the first Zener diode, the second drain of the second transistor, and a second cathode of the second Zener diode.

4. The ultrasound system of claim 3, wherein the plurality of transistors includes the first transistor, the second transistor, a third transistor, and a fourth transistor, and wherein a first gate of the first transistor is directly electrically coupled to each of the second drain of the second transistor and a second anode of the second Zener diode, a second gate of the second transistor is directly coupled to each of the first drain of the first transistor and a first anode of the first Zener diode, a third gate of the third transistor is directly electrically coupled to the first anode of the first Zener diode, and a fourth gate of the fourth transistor is directly electrically coupled to a second positive input voltage of the one or more voltage inputs.

5. The ultrasound system of claim 4, further comprising each of a fifth transistor, a sixth transistor, a seventh transistor, and an eighth transistor, wherein a fifth gate of the fifth transistor is directly electrically coupled to an eighth gate of the eighth transistor, wherein a fifth source of the fifth transistor is directly electrically coupled to a seventh drain of the seventh transistor, and wherein a fifth drain of the fifth transistor is directly electrically coupled to each of the second anode of the second Zener diode and the second drain of the second transistor.

6. The ultrasound system of claim 5, wherein a sixth gate of the sixth transistor is directly electrically coupled to a seventh gate of the seventh transistor, wherein a sixth source of the sixth transistor is directly electrically coupled to the seventh drain of the seventh transistor, and wherein a sixth drain of the sixth transistor is electrically directly coupled to each of a third drain of the third transistor of the plurality of transistors, the first anode of the first Zener diode, and the third gate of the third transistor.

7. The ultrasound system of claim 6, wherein the seventh gate of the seventh transistor is directly electrically coupled to the sixth gate of the sixth transistor, wherein the seventh drain of the seventh transistor is directly electrically coupled to the sixth source of the sixth transistor and a first end of a first capacitor, and wherein a seventh source of the seventh transistor is directly electrically coupled to a ground line and a second end of the first capacitor.

8. The ultrasound system of claim 7, wherein the eighth gate of the eighth transistor is directly electrically coupled to the fifth gate of the fifth transistor, and wherein an eighth drain of the eighth transistor is directly electrically coupled to the sixth source of the sixth transistor and a first end of a second capacitor, and wherein the seventh source of the seventh transistor is directly electrically coupled to a ground line and a second end of the second capacitor.

9. The ultrasound system of claim 8, wherein the one or more voltage inputs includes a positive voltage input configured to send a positive voltage logical control pulse to gates of each of the fifth transistor and the eighth transistor, and an inverted positive voltage input configured to send a second positive voltage logical control pulse to gates of each of the sixth transistor, the seventh transistor, and the fourth transistor.

10. The ultrasound system of claim 9, further comprising a fourth source of the fourth transistor, the fourth source directly electrically coupled to the second end of the first capacitor, the second end of the first capacitor directly electrically coupled to the ground line.

11. The ultrasound system of claim 4, wherein an input of the ultrasound transducer is directly electrically coupled to each of a third drain of the third transistor and a fourth drain of the fourth transistor.

12. The ultrasound system of claim 1, wherein the positive high voltage circuit is electrically coupled to and configured to drive the ultrasound transducer at positive high voltage, and the negative high voltage circuit is electrically coupled to and configured to drive the ultrasound transducer at negative high voltage, and wherein the positive high voltage circuit includes a second positive high voltage power supply of the one or more high voltage power supplies, the second positive high voltage power supply configured to supply power to the positive high voltage circuit, and wherein the negative high voltage circuit includes a third negative high voltage power supply of the one or more high voltage power supplies, the third negative high voltage power supply configured to supply power to the negative high voltage circuit.

13. A method for a pulse circuit coupled to an ultrasound transducer of an ultrasound system, the method comprising:
  switching on a positive high voltage supply of the pulse circuit, the positive high voltage supply coupled to a third source of a third transistor;
  sending a first positive voltage logical control pulse to a sixth gate of a sixth transistor of the pulse circuit, the first positive voltage logical control pulse generating a current between a sixth drain and sixth source of the sixth transistor;
  flowing a first dynamic current from a third gate of the third transistor of the pulse circuit, the first dynamic current switching on the third transistor, the first dynamic current flowing through the sixth drain and the sixth source of the sixth transistor to a first capacitor, and charging the first capacitor; and
  driving the ultrasound transducer coupled to a third drain of the third transistor at a first voltage of the third drain of the third transistor, the first voltage equal to a second voltage of the positive high voltage supply, the first voltage generated in response to the switching on of the third transistor via the first dynamic current.

14. The method of claim 13, further comprising sending the first positive voltage logical control pulse to a seventh gate of a seventh transistor of the pulse circuit, and allowing discharge of a second capacitor placed between a seventh source and a seventh drain of the seventh transistor.

15. The method of claim 14, wherein driving of the ultrasound transducer at the second voltage of the positive high voltage supply is activated in response to the third transistor being switched on, wherein the third transistor being switched on in response to the first dynamic current charging the first capacitor to a threshold level, the threshold level estimated based on a bias voltage of the third transistor.

16. The method of claim 15, further comprising:
  upon completion of generation of the first positive voltage logical control pulse, sending a second inverted positive voltage logical control pulse to each of a fourth gate of a fourth transistor and a fifth gate of a fifth transistor of the pulse circuit, the second inverted positive voltage logical control pulse generating a current between a fifth drain and a fifth source of the fifth transistor;
  flowing a second dynamic current from a first gate of a first transistor of the pulse circuit, the second dynamic current switching on the first transistor, the second dynamic current flowing through the fifth drain and the fifth source of the fifth transistor to the second capacitor, and charging the second capacitor; and
  driving the ultrasound transducer coupled to a fourth drain of the fourth transistor at a third voltage equal to ground via the fourth transistor, the third voltage at the fourth transistor generated in response to the switching on of the fourth transistor via second positive voltage logical control pulse received at the fourth gate of the fourth transistor.

17. The method of claim 16, further comprising sending the second inverted positive voltage logical control pulse to an eighth gate of an eighth transistor of the pulse circuit, allowing discharge of the first capacitor placed between an eighth source and an eighth drain of the eighth transistor.

18. The method of claim 17, wherein driving of the ultrasound transducer at ground via the fourth transistor is initiated by the second inverted positive voltage logical control pulse being received at the fourth gate of the fourth transistor and following switching off of the third transistor, the third transistor being switched off in response to the first transistor being switched on, the first transistor being switched on in response to the second dynamic current charging the second capacitor to a threshold level, and wherein the threshold level is determined by a bias voltage of the first transistor.

19. An ultrasound system comprising:
  an ultrasound transducer configured to generate acoustic ultrasonic pulses in response to electronic driving; and
  a pulse circuit electrically coupled to and configured to drive the ultrasound transducer, the pulse circuit further comprising:
    one or more voltage inputs configured to generate logical control pulses within the pulse circuit;
    one or more high voltage power supplies configured to supply power to the pulse circuit;
    a plurality of transistors, the plurality of transistors configured to drive the ultrasound transducer in response to dynamic currents generated at gates corresponding to one or more of the plurality of transistors; and
    a first diode included between a first source and a first drain of a first transistor and a second diode included between a second source and a second drain of a second transistor,
  wherein the pulse circuit is a three-level pulse circuit, including a positive high voltage circuit and a negative high voltage circuit, the positive high voltage circuit electrically coupled to and configured to drive the ultrasound transducer at positive high voltage, and the negative high voltage circuit electrically coupled to and configured to drive the ultrasound transducer at negative high voltage.

* * * * *